US010488247B2

(12) United States Patent
Varghese et al.

(10) Patent No.: US 10,488,247 B2
(45) Date of Patent: Nov. 26, 2019

(54) METHOD AND APPARATUS FOR RAPID ACQUISITION OF ELASTICITY DATA IN THREE DIMENSIONS

(71) Applicant: Wisconsin Alumni Research Foundation, Madison, WI (US)

(72) Inventors: Tomy Varghese, Madison, WI (US); Atul Nishikant Ingle, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 974 days.

(21) Appl. No.: 14/276,019

(22) Filed: May 13, 2014

(65) Prior Publication Data

US 2015/0330832 A1  Nov. 19, 2015

(51) Int. Cl.
| | |
|---|---|
| *G01H 17/00* | (2006.01) |
| *A61B 18/14* | (2006.01) |
| *A61B 8/08* | (2006.01) |
| *A61B 8/00* | (2006.01) |
| *A61B 18/00* | (2006.01) |

(52) U.S. Cl.
CPC ............. *G01H 17/00* (2013.01); *A61B 8/085* (2013.01); *A61B 8/466* (2013.01); *A61B 8/485* (2013.01); *A61B 8/5207* (2013.01); *A61B 18/1482* (2013.01); *A61B 8/0841* (2013.01); *A61B 8/4461* (2013.01); *A61B 2018/00577* (2013.01); *A61B 2018/00994* (2013.01)

(58) Field of Classification Search
None
See application file for complete search history.

(56) References Cited

U.S. PATENT DOCUMENTS

| | | | |
|---|---|---|---|
| 4,341,120 A | 7/1982 | Anderson | |
| 5,159,931 A | 11/1992 | Pini | |
| 6,228,028 B1 | 5/2001 | Klein et al. | |
| 7,166,075 B2 | 1/2007 | Varghese et al. | |
| 7,302,092 B1 | 11/2007 | Fenster et al. | |
| 7,632,230 B2* | 12/2009 | Varghese | A61B 8/08 |
| | | | 600/407 |
| 7,903,113 B2* | 3/2011 | Krishnan | G06T 15/08 |
| | | | 345/419 |

(Continued)

FOREIGN PATENT DOCUMENTS

KR   1020120107053 A   9/2012

OTHER PUBLICATIONS

Thune et al., "Practical method for estimating enclosed volumes using 3D ultrasound" European Journal of Ultrasound 3 (1996) 83-92.*

(Continued)

*Primary Examiner* — John C Kuan
(74) *Attorney, Agent, or Firm* — Boyle Fredrickson, S.C.

(57) ABSTRACT

Interpolation of ultrasound data at regular grid locations is provided by simultaneously optimizing interpolated data according to fidelity of interpolation of the voxel data to actual measured spatial data and according to a gradient of the interpolated data. This process is made amenable to real-time processing by limiting the range of interpolation to produce a sparse interpolated matrix that may be readily inverted. Artifacts and inefficiencies from successive stages of interpolation and data smoothing are thereby avoided.

21 Claims, 5 Drawing Sheets

(56) References Cited

U.S. PATENT DOCUMENTS

| | | | |
|---|---|---|---|
| 8,328,726 B2 | 12/2012 | Varghese et al. | |
| 2005/0043619 A1 | 2/2005 | Sumanaweera et al. | |
| 2007/0287902 A1* | 12/2007 | Fuimaono | A61B 5/055 600/300 |
| 2010/0240996 A1 | 9/2010 | Ionasec et al. | |
| 2010/0256530 A1* | 10/2010 | Varghese | A61B 5/015 600/587 |
| 2012/0128223 A1 | 5/2012 | Rivaz et al. | |
| 2012/0235998 A1* | 9/2012 | Smith-Casem | G01S 15/8993 345/424 |
| 2013/0004052 A1 | 1/2013 | Chen et al. | |

OTHER PUBLICATIONS

Victor Torrealba, Antonio Bosnjak, Manuel Acuna, Lilia Hernandez Lilia, Christian Roux, Guillermo Montilla, 3D Dynamics echocardiography. Workstation for the acquisition, reconstruction and visualization of 4D images of the heart; Ier. Congreso Virtual de Cardiologia—Temas Libres Premiados—Torr . . . , Publicacion Sep. 2000; Webmaster—Actualizacion: 06-Ene-2005; p. 1-4; Venezuela.
International Search Report; International application No. PCT/US2015/020943; Filing Date: Mar. 17, 2015.

* cited by examiner

METHOD AND APPARATUS FOR RAPID ACQUISITION OF ELASTICITY DATA IN THREE DIMENSIONS

STATEMENT REGARDING FEDERALLY SPONSORED RESEARCH

This invention was made with government support under CM 12192 awarded by the National Institutes of Health. The government has certain rights in the invention.

CROSS-REFERENCE TO RELATED APPLICATIONS

--

BACKGROUND OF THE INVENTION

The present invention relates to ultrasonic imaging techniques for obtaining information about tissue elasticity and in particular to a method of rapidly acquiring three-dimensional elasticity reconstructions useful, for example, during RF ablation.

Elastography is an imaging modality that reveals the stiffness properties of tissues, for example, axial strain, lateral strain. Poisson's ratio, shear wave velocity, shear and Young's moduli, or other common stiffness measurements. The stiffness measurements may be output as quantitative values or mapped to a gray or color scale to form a picture over a plane or within a volume.

Generally, stiffness is deduced by monitoring tissue movement under an applied quasi-static or dynamic force or deformation. The monitoring may be done by any medical imaging modality including computed tomography (CT), magnetic resonance imaging (MRI), and ultrasonic imaging. Elastography of this type is analogous to a physicians palpation of tissue in which the physician determines stiffness by pressing the tissue and detecting the amount that the tissue yields under pressure.

In "dynamic" elastography, a low frequency vibration is induced in the tissue and the velocity of the resulting compression/shear waves are tracked and measured, for example, using ultrasonic Doppler detection. In "quasi-static" elastography, two images of the tissue are obtained at different states of compression, typically using the ultrasonic transducer as a compression paddle. Displacement of the tissue between the two images is used to deduce the stiffness of the tissue.

Ideally, elasticity data is acquired over a volume of interest in the tissue, U.S. patent application Ser. No. 13/780,880, filed Feb. 28, 2013, assigned to the same assignee as the present invention and hereby incorporated by reference, describes a system for volumetric ultrasound acquisition which obtains data in a series of radially extending planes positioned at different angles about a common axis.

With most acquisition patterns, spatial data must be interpolated to regular voxel points along a regular grid so that the data may be displayed through projections as pixels on a display monitor. In the acquisition pattern of radially extending planes described above, data on any of the planes may be first interpolated to regular grid locations within the plane and then interpolation may be conducted between the interpolated data of different planes.

The spatial data may be relatively noisy and accordingly, within each plane, the spatial data may first be fit to a model, for example, extracting trends from the data that reduce image artifiicts caused by noise.

SUMMARY OF THE INVENTION

Employing two distinct steps of modeling then interpolating is both time-consuming and may produce a suboptimal fit of the voxel data to the spatial data. Ideally, these processes could be performed simultaneously in three dimensions to better accommodate the trade-off between interpolation fidelity and noise reduction. Generally, global optimization techniques, such as linear programming, can be extremely time-consuming when the number of interpolation grid points is large, and accordingly impractical for generating real-time ultrasound images.

The present invention addresses these problems by allowing simultaneous three-dimensional interpolation and noise reduction by formulating the problem as a smoothness-constrained trilinear interpolation considering only locally adjacent spatial data points. This problem formulation provides a sparse matrix that may be readily inverted providing a simple closed-form solution that allows the steps of interpolation and noise reduction to be reliably and rapidly executed. Additional time savings can be obtained by separately evaluating subregions of the volume of interest and then joining the subregions together by a simple weighting process.

Specifically then, in one embodiment, the invention provides apparatus for acquiring three-dimensional ultrasound data including an ultrasonic probe assembly adapted to direct an ultrasound beam into tissue and receive ultrasonic echoes and measure the same to provide ultrasound data, and an electronic computer receiving the ultrasound data and executing a stored program held in non-transitive medium.

The program executes to process the ultrasound data to obtain spatial data characterizing the tissue at a plurality of discrete locations over three dimensions of a volume of interest within the tissue followed by a determination of the values of voxels in a three-dimensional image grid within the tissue. This determination simultaneously minimizes a combination of an error between each given voxel data and interpolated values of the spatial data selected to be in a region proximate to the voxel data; and a gradient of the voxel data at the given voxel data point location. The region proximate to the voxel data volume is three-dimensional but limited in extent to much less than the dimensions of the entire volume of interest.

It is a feature of at least one embodiment of the invention to provide improved processing of sparse and noisy ultrasound data in a way that simultaneously accommodates an interpolation and smoothing of the data in three dimensions.

The interpolation error considered in this process may be a function of a magnitude of a difference between the value of a given element of spatial data and an interpolated value of the surrounding voxels to the location of the spatial data in three dimensions.

It is thus a feature of at least one embodiment of the invention to provide a simple measure of interpolation fidelity.

The gradient may be a function of differences among values of adjacent voxel data to the given voxel.

It is thus a feature of at least one embodiment of the invention to provide an easily calculated measure of smoothness in the image.

The determination may be performed by selecting a value of each given voxel data to minimize:

$$\|Ac-b\|^2$$

subject to $$\|Bc\|^2 \leq M$$

where: c is the data of the given voxels;
b is the ultrasonically measured spatial data;
A is an interpolant matrix performing a linear interpolation of values in c to the locations of data points in b;
B is a finite differencing gradient matrix representing the gradient in voxel data values at c; and
M is a constant selected to describe the desired image smoothness.

It is thus a feature of at least one embodiment of the invention to provide a technique for providing a balancing between interpolation fidelity and smoothness in three dimensions for all voxels.

The matrix A may be a sparse matrix.

It is thus a feature of at least one embodiment of the invention to provide a technique well suited to the image processing of sparse ultrasound data which yields a readily invertible matrix.

The determination may solve the closed form expression:

$$c = (A^T A + \lambda B^T B)^{-1} A^T b$$

where $\lambda$ is a predetermined value controlling the amount of smoothing of the data.

It is thus a feature of at least one embodiment of the invention to provide a tractable, closed-form expression for rapidly implementing the present invention.

The number of points of spatial data within the volume of interest may be less than the number of voxels within the volume of interest.

It is thus a feature of at least one embodiment of the invention to provide a technique that may work with ill-posed inverse problems that have fewer data points than the number of voxels.

The region proximate to the data volume may extend only to the closest eight voxels in case of trilinear interpolation. Alternatively or in addition, the voxel data may provide points at regular intervals along three Cartesian dimensions and the region proximate to the voxel data may be a smallest polyhedron that surrounds the spatial data point with voxels at vertex points and wherein the error is calculated only from interpolation at these vertex points.

It is thus a feature of at least one embodiment of the invention to create a tractable matrix expression by limiting the spatial scope of the interpolation function.

The interpolated values may be trilinear interpolation in three dimensions.

It is thus a feature of at least one embodiment of the invention to employ a well-behaved interpolation system that may be spatially limited without undue artifacts.

The volume of interest may be subdivided into sub-blocks and the above process repeated for multiple sub-blocks and those sub-blocks combined by weighting data at the periphery of adjacent sub-blocks.

It is thus a feature of at least one embodiment of the invention to permit the optimization process to be performed in available high-speed computer memory (without, for example, disk drive accesses) for high speed commensurate with the need for real time data display.

The spatial data characterizing the tissue may be a speed of a shear wave through the tissue at the points of spatial data or a function of displacement of the tissue in response to a quasi-static periodic compression of the tissue.

It is thus a feature of at least one embodiment of the invention to provide image processing for standard elastography ultrasound acquisitions.

These particular objects and advantages may apply to only some embodiments falling within the claims, and thus do not define the scope of the invention.

DETAILED DESCRIPTION OF THE PREFERRED EMBODIMENT

General Description of the Hardware

Figure 1:
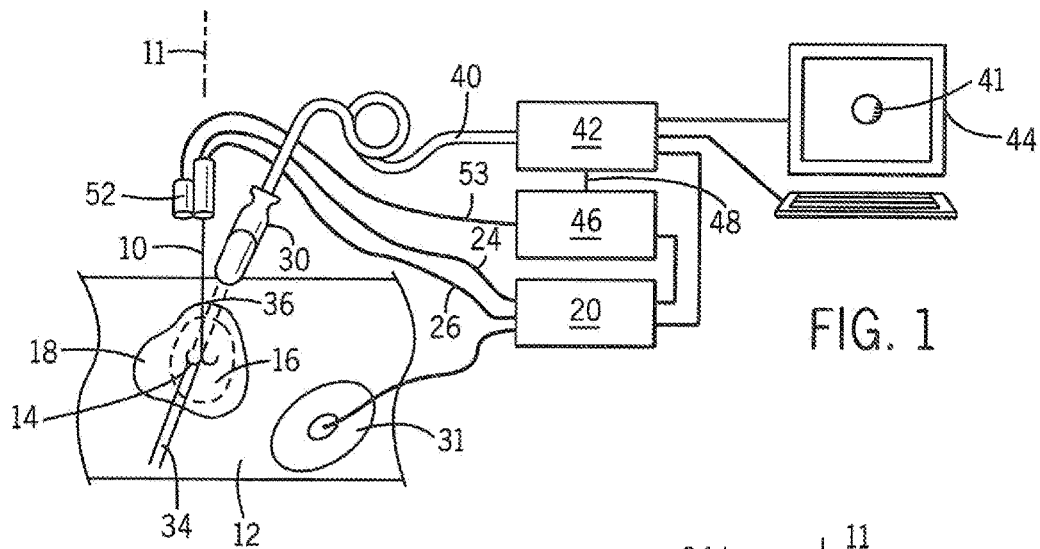
FIG. 1 is a simplified block diagram of an ultrasound imaging system for use with the present invention using a standard 2-D array ultrasound transducer as used with an optional RF ablation system providing an ablation probe for introduction into a tumor site of an in vivo organ and including a control system for applying a controlled reciprocation RF ablation probe for shear wave or quasi-static elastography imaging.

Referring now to FIG. 1, an RF or microwave ablation probe 10 may be inserted percutaneously into a patient 12 along an axis 11 to have its tip located at an ablation region 16 within an organ 18, such as the liver. Extensible electrode tines 14, at the tip of the probe 10, may grip the tissue of the ablation region and provide a greater area of electrical contact to conduct ablative current from a radiofrequency (RF) source 20.

In this regard, electrical energy from the RF source 20 is conducted through an insulated shaft of the probe 10 to the conductive tines 14 where ionic heating of the tissue kills tumor tissue. A large-area grounding pad 31 placed on the patient's skin provides a return path for this current. The tines 14 may optionally include thermocouples for temperature measurements used to control the electrical energy to minimize the formation of a layer of high impedance charred tissue between the tines 14 and the tissue.

RF ablation probes 10 suitable for this purpose may include a single 17-gauge electrode, with a 2-3 cm long electrically active region at the tip embedded in tissue. These electrodes also offer the option of internally circulating chilled water during the ablation procedure to minimize the charring of tissue adjacent to the electrically active region of the electrode. RF ablation probes 10 of this kind having extensible tines and thermocouple sensors are known in the art and commercially available, for example, under the tradename Valleylab Cool-Tip™ ablation electrode manufactured by Valleylab, CO, USA, or from other companies. The RF source 20 may be a Rita Model 30 electrosurgical device manufactured by Rita Medical Systems, Inc., Mountain View, Calif., or another similar device.

During the ablation process, electrical current is conducted from the RF source 20 along line 26 to the ablation probe 10. The temperature signal is returned along line 24 to be received by the RF source 20 and used to limit the temperature of ablation according to techniques well understood in the art.

Imaging of the tissue and the tip of the probe 10 may be done using standard ultrasonic imaging system hardware, for example, the Siemens S2000 Real Time Scanner manufactured by Siemens, Inc. of California. The ultrasonic imaging system hardware may include an ultrasonic transducer 30 communicating with ultrasound processing circuitry 42. The ultrasonic transducer 30 may be, for example, a one-dimensional ultrasonic transducer 30 (meaning that it has a one-dimensional array of individual transducer elements to acquire data over two dimensions) in the form of a linear array transducer approximately forty millimeters wide, operating with dynamic focus over a forty percent bandwidth and producing signals at a center frequency of five megahertz.

During insertion of the probe 10, the ultrasound transducer 30 is placed against the skin of the patient 12 to emit a beam 36 of ultrasound directed into the patient 12 to acquire echo data along an imaging or data plane 34 extending from the ultrasound transducer 30 (seen edgewise in FIG. 1). After insertion of the probe 10, the ultrasound transducer 30 may be used to monitor the ablation using elastographic imaging as will be described. During this monitoring and the subsequent elastographic imaging, the axis of the ultrasound transducer along which the ultrasound beam 36 propagates is aligned as closely as possible to the axis 11 along which the probe 10 extends. The probe 10 stabilizes the organ 18 and prevents lateral shifting along an axis perpendicular to axis 11.

During both insertion of the probe 10 and the ablation process, an ultrasound beam 36 generated by the ultrasound transducer 30 travels into the tissue of the patient 12 and is reflected at various tissue structures and boundaries. These echoes are detected by the ultrasound transducer 30 and conducted by cable 40 to the ultrasound processing circuitry 42. The received signals are digitized at a sampling rate of approximately 50 megahertz and then processed according to techniques well known in the art to produce a sequence of two-dimensional images, for example, providing a constantly refreshed B-mode image on display terminal 44.

A controller 46, which may be a computer or logic controller programmed as described below, may also provide output lines 53 connected to a motorized carriage 52, for example, using a motor and a lead screw (not shown) to provide motion of the probe 10 along its insertion axis 11 to reciprocate the probe 10 in a controlled manner according to signals on output line 53 as will also be described. Other mechanisms for implementing the motorized carriage 52, including those which apply a predetermined compressive force or low-frequency oscillation, are also contemplated, for example, using an eccentric weight. In some embodiments, the controller 46 may also communicate with ultrasound processing circuitry 42 (or the display terminal 44 directly) for displaying images and receiving user input commands.

The digitized echo signals from the ultrasound transducer 30 are further processed either within the ultrasound processing circuitry 42, or within controller 46, to produce an elastographic image 41. In the former case, line 48 communicates signals from the controller 46 to the ultrasound processing circuitry 42 to coordinate generation of the elastographic image; in the latter case, line 48 carries the control signals and digitized echo signals from the ultrasound processing circuitry 42 to the controller 46 for processing by the controller 46.

Data Acquisition

Figure 2:
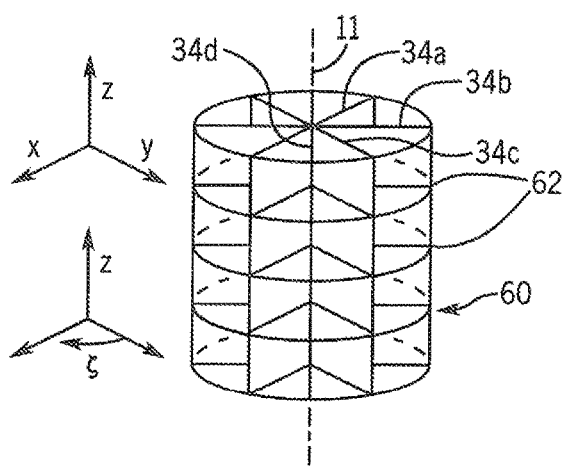
FIG. 2 is a simplified depiction of a geometry of a pattern of data acquisition that may be employed in the present invention showing an example with three angularly separated planes of data acquisition sharing a common axis.

Referring now to FIGS. 1 and 2, in a first embodiment, the ultrasound transducer 30 may be rotated about the probe 10 so as to rotate the data plane 34 about axis 11 while maintaining the plane 34 substantially aligned with axis 11. This rotation allows the acquisition of echo data along multiple planes. In this example four planes 34*a-d* are shown spaced from each other by 45 degrees. Other numbers of planes, for example, five and six equally or unequally spaced planes 34, are also practical and there is generally no upper limit to the number of planes based on a trade-off between data acquisition and speed of reconstruction. Each of these planes 34 will provide multiple points of echo data over the surface of the plane 34, each point of echo data described, for example, by a z-axis coordinate value (where the z-axis is aligned with axis 11) and an x-axis coordinate value perpendicular to the z-axis and lying within the plane 34. Together the planes 34*a-d* are circumscribed within a cylindrical volume 60 that holds multiple C-planes 62 generally normal to axis 11 and spaced regularly along the z-axis. Generally, these planes may be acquired by beam steering or other techniques.

Figure 8:
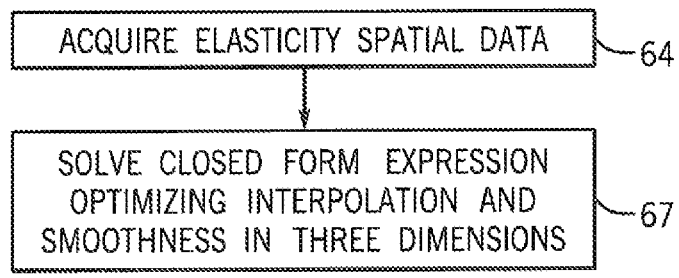
FIG. 8 is a simplified flowchart depicting the principal steps of the present invention in several embodiments.

Referring momentarily to FIG. 8, in a first step of the invention, echo data of each plane 34 is processed to extract raw data necessary for elasticity measurements as indicated by process block 64. The deduced elasticity may indicate absolute or relative elasticity of the tissue, and the raw data may be obtained using various different techniques. In a first technique, the data of the planes 34 may be processed to acquire multicycle shear wave data as will now be described.

Figure 3:
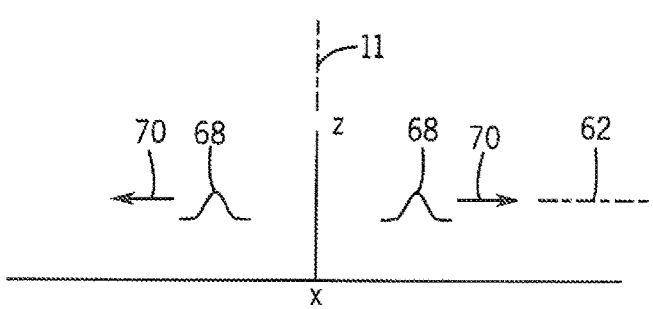
FIG. 3 is a graph of the shear wave propagation along an x-axis as depicts noise in the data that can create artifacts during interpolation.
Figure 3:
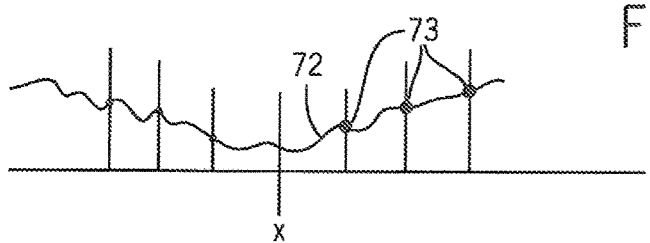

Referring to FIGS. 1 and 3, a reciprocating motion of the probe 10, or other stimulation techniques such as ARFI, SSI and EVE and the like, may generate shear waves 68 propagating perpendicularly to axis 11, for example, radially away from that axis 11 as indicated by arrows 70. Detection of the shear waves at each C-plane 62 may be performed by direct analysis of the radiofrequency ultrasonic signal or through the analysis of B-mode images to detect the displacement between successive images incident to the deformation of the shear wave 68, for example, as described in U.S. Pat. No. 8,328,726 cited above. Generally the generation of B-mode imaging will not occur rapidly enough to track movement of the shear waves 68 along arrows 70 in real time but an effective reconstruction of that motion may be obtained by coordination between ultrasound processing circuitry 42 and the controller 46 reciprocating the probe 10 to obtain data of the data plane 34 capturing the shear waves 68 at multiple times, each time having a different phase delay with respect to the reciprocation of the probe 10. Under the assumption that the shear waves 68 will be identical for each cycle of the reciprocation, this allows a piecewise reconstruction of the motion of the shear wave 68. Alternatively, the entire image plane can be scanned using a plane acoustic wave to bypass the low imaging speed of B-mode acquisitions. Such plane acoustic wave acquisitions image the complete imaging plane in a single sweep, unlike the sequential focused technique used in B-mode acquisitions.

Propagation of the shear wave 68 in terms of arrival time at various locations along the x-axis may be plotted in a measurement curve 72 for each C-plane against different positions along the x-axis. The reciprocal of the slope of the measurement curve 72 will generally indicate the velocity of the shear wave 68 providing information about elasticity of the propagating medium. The substantial noise component in the measurement curve 72 presents a problem with respect to differentiating this measurement curve 72 in order to obtain velocity. Samples 73 of this measurement curve 72 will be acquired per process block 64 of FIG. 8 to be discussed below.

Figure 4:
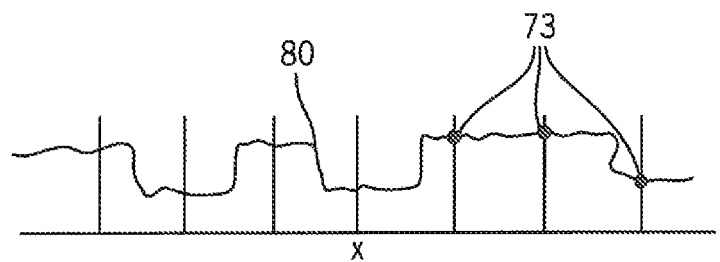
FIG. 4 is a graph similar to that of FIG. 3 showing tissue displacement at different points along the x-axis associated with quasi-static elastography and corresponding noise.

Referring now to FIGS. 4 and 8, in an alternative technique, the acquired ultrasound data at process block 64 may indicate a z-axis displacement of the tissue with reciprocation of the probe along axis 11 or other stimulation of the tissue along axis 11; for example, ultrasonic stimulation may be used to deduce tissue movement within a cycle of stimulation according to standard dynamic or quasi-static elastography. Again, a measurement curve 80 providing a measure along the x-axis for each C-plane 62 may be obtained and sampled to provide for the acquired elasticity data at process block 64 of FIG. 8.

Determining Voxel Data

Figure 5:
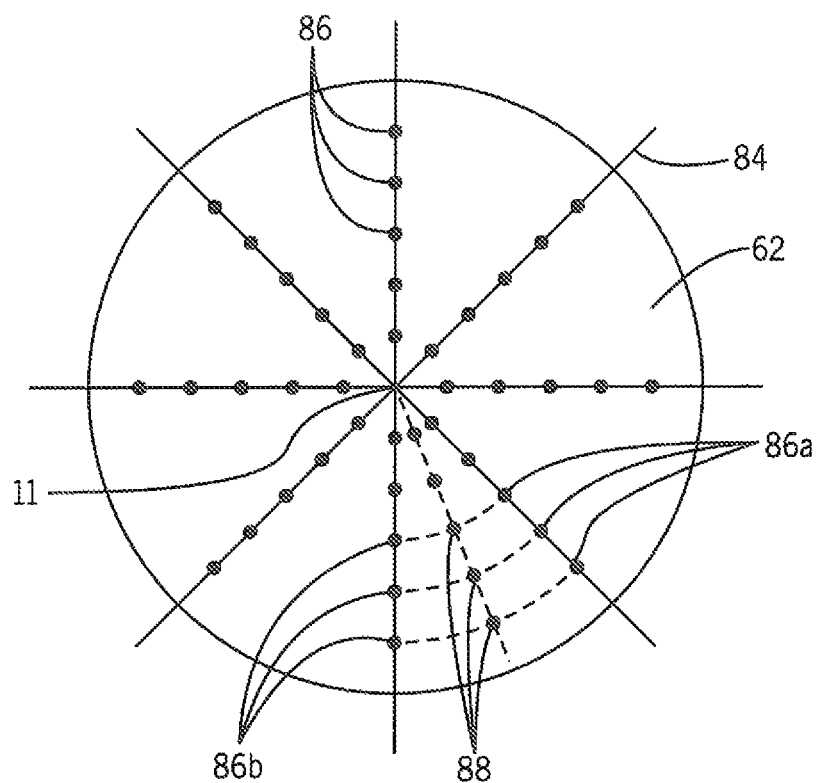
FIG. 5 is a top plan view of the data acquisition geometry of FIG. 2 showing bilinear cylindrical interpolation used in one embodiment of the invention over four angularly separated planes.

Referring now to FIGS. 5 and 8, the samples 73 may lie along intersection lines 84 between the planes 34 and each C-plane 62 to provide for multiple points of elasticity spatial data 86 spaced along each of the lines 84 within each C-plane 62. This acquired data of the samples 73 will be termed "spatial data" and designated by values "b" to distinguish it from data of voxels which will be determined from the spatial data and designated by values "c".

Generally, the present invention determines values of the voxels 88 so that when the values of the voxels 88 are interpolated to the locations of actual spatial data 86, the two values match (interpolation fidelity). The interpolation may use, for example, a trilinear interpolation among the voxels 88 surrounding given spatial data 86.

As will be seen, this interpolation fidelity is balanced against a requirement for smoothness in the data of the voxels 88, meaning generally that the data of the voxels 88 changes slowly over space in the manner to be expected when measuring the elastic properties of physical tissue which will tend to be homogenous within any given region.

Figure 11:
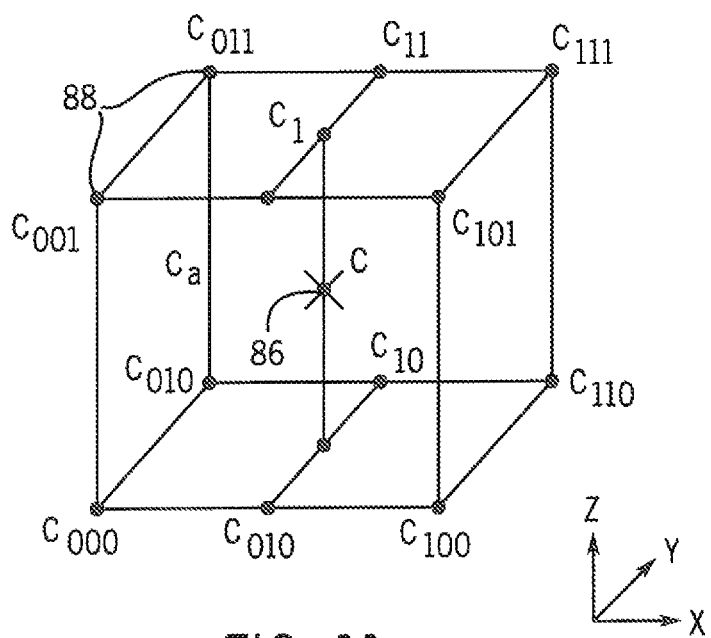
FIG. 11 is a diagram showing adjacent spatial data points showing values used for the interpolation of voxel data to measured spatial data.

Referring now to FIG. 11, an element of spatial data 86 may be compared to a trilinear interpolation of the data of voxels 88 as shown as the vertices of a simple polyhedron (e.g., a cube) surrounding the element of spatial data 86. As is understood in the art, trilinear interpolation will first perform linear interpolation, for example, between voxels 88 at points cool and coo, being two vertices of the polyhedron, to obtain a value $c_{01}$ along one edge of the polyhedron between the two vertices at a location along the edge generally aligned with one coordinate of the spatial data 86—in this case the x-coordinate. Similar interpolation is conducted for each edge of the polyhedron parallel to the above edge to obtain first interpolation values $c_{11}$, $c_{00}$, $c_{10}$. Linear interpolation is then performed between corresponding pairs of these interpolated values to provide second interpolation values ($c_1$, $c_0$) aligned with a second coordinate of the spatial data 86—in this case the y-coordinate. Finally the third interpolation will be performed between the second interpolated values to provide a third interpolation value c for the spatial data 86. The difference between this third interpolation value c and the actual spatial data 86 will desirably be minimized.

Generally this interpolation process can be represented as follows:

$$c = k_{000}c_{000} + k_{001}c_{001} + \ldots + k_{111}c_{111} \quad (1)$$

where the coefficients k are interpolation weights that may be collected into a matrix A having eight non-zero entries in each row corresponding to the eight interpolation weights; the number of rows equal to the number spatial data points; and the number of columns equal to the number of voxels.

Figure 10:
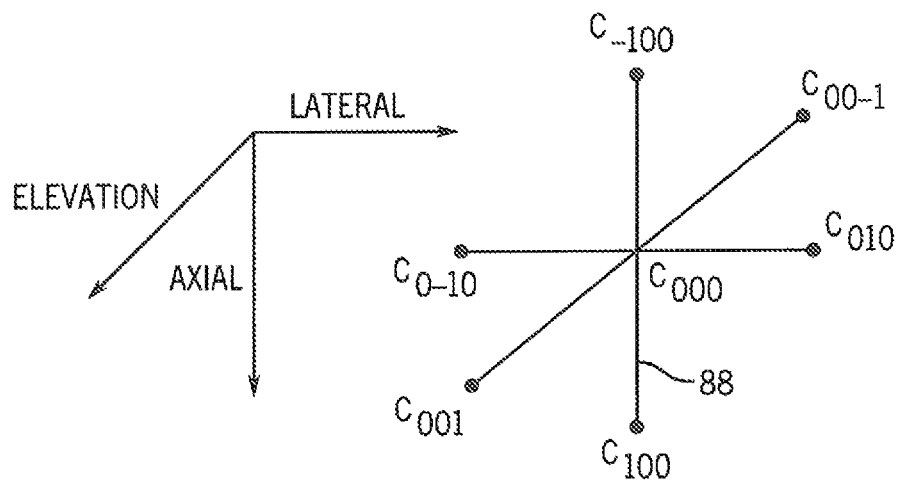
FIG. 10 is a diagram of adjacent data voxels showing the values used for the calculation of an approximation of gradient at a given voxel.

Referring now to FIG. 10, the present invention also seeks to enforce smoothness on the selected values of voxels 88. In one embodiment, the smoothness may be enforced by constraining the second derivative (Laplacian) at each of the voxel values. The second derivative can be approximated by the second order central differences as follows:

$$\frac{d^2c}{dx^2}(x, y, z) \approx c_{011} - c_{00-1} + 2c_{000} \quad (2)$$

$$\frac{d^2c}{dy^2}(x, y, z) \approx c_{010} - c_{0-10} + 2c_{000} \quad (3)$$

$$\frac{d^2c}{dz^2}(x, y, z) \approx x_{100} - x_{-100} + 2x_{000}. \quad (4)$$

The Laplacian is then given by:

$$\nabla^2 c = \frac{d^2c}{dx^2} + \frac{d^2c}{dy^2} + \frac{d^2c}{dz^2} \quad (5)$$

where the coefficients of equations (2)–(4) of +1, −1, and 2 may be entered into a matrix B so that the matrix vector product Bc provides the vector of the Laplacian derivative over the entire grid. Matrix B will generally be a square matrix with seven non-zero entries per rows and the number of columns equal to the number of voxels.

The present invention may then compute the values c for each voxel by choice of c to minimize:

$$\|Ac - b\|^2 \quad (6)$$

subject to $$\|Bc\|^2 \leq M \quad (7)$$

where:
c is the voxel data to be determined;
b is the known spatial data proximate to the voxels;
A is an interpolant matrix performing a linear interpolation of values c to the location of data points in b;
B is a finite differencing gradient matrix providing the gradient in data of the voxels; and
M is a constant selected to describe the desired image smoothness.

Here the symbol ∥ ∥ denotes the 2-norm of the vector (i.e., the square root of the sum of the square of the entries).

An unconstrained version of this minimization problem may be represented as follows:

$$\text{minimize}_x \|Ac-b\|^2 + \lambda \|Bc\|^2 \quad (8)$$

where λ provide a weighting rather than a hard limit. This problem of equation (8) has a closed form solution given by:

$$c = (A^T A + \lambda B^T B)^{-1} A^T b \quad (9)$$

where $^T$ denotes a matrix transposition.

This matrix inverse is not explicitly calculated, but instead a sparse linear solver routine may be used which solves the system of equations:

$$(A^T A + \lambda B^T B)c = A^T b \quad (10)$$

for the unknowns in c. The system of equations can be solved rapidly even for large grid sizes with over 1 million grid points because the matrices are sparse with only a few nonzero entries near the diagonal (also called a banded diagonal structure). The banded diagonal structure is a consequence of the vectorization of the 3-D points into a one-dimensional vector c.

While the value of λ may be predetermined it will be understood that it may also be selected by cross-validation of the data, without the user having to specify the value of λ in advance.

Referring now to FIG. 8, this solution process is indicated generally by process block 67.

Figure 9:
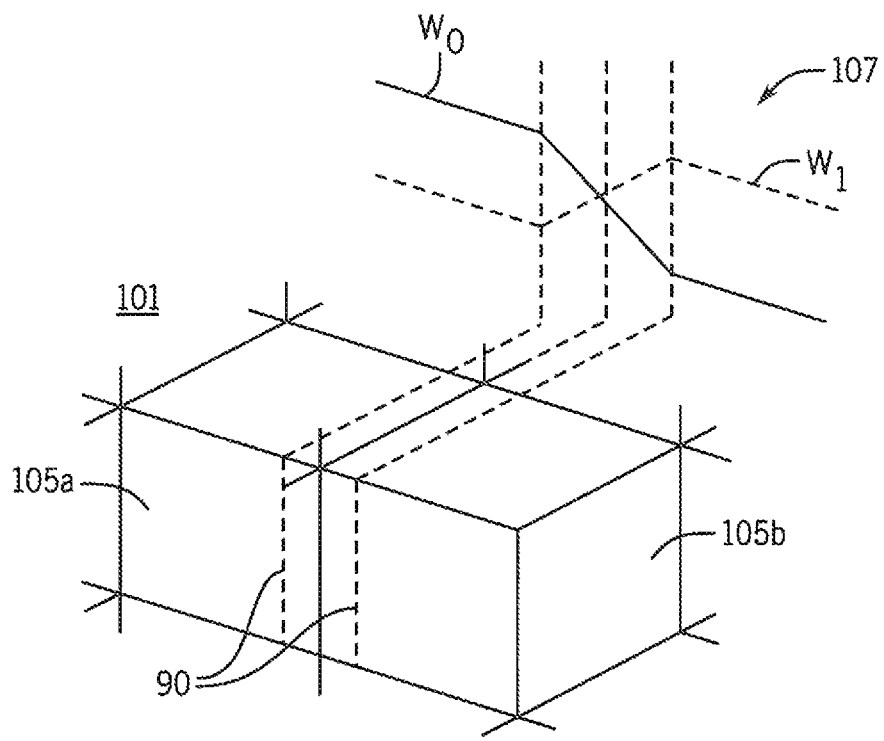
FIG. 9 is a perspective diagram of two sub-blocks of the volume of interest attached together by a weighting process.

Referring now to FIG. 9, the ability to rapidly solve equation (10) can be enhanced by allowing all of the necessary matrix and vector values to be stored in low latency memory (e.g., RAM). This can be ensured by dividing a region of interest 101 encompassing all of the relevant spatial data b into one or more sub-blocks 105a, 105b, etc. and by separately processing each sub-block 105 with equation (10). The sub-blocks may then be "stitched" together by blending peripheral voxel data 90 (representing overlapping spatial locations) using, for example, weighting values 107 of $w_0$ and $w_1$ on respective sub-blocks 105, each weight slowly decreasing the weighting of the data of one sub-block 105 as one moves toward the adjacent sub-block 105. In this regard, the two weighting values 107 may be selected so that they always sum to unity.

Figure 6:
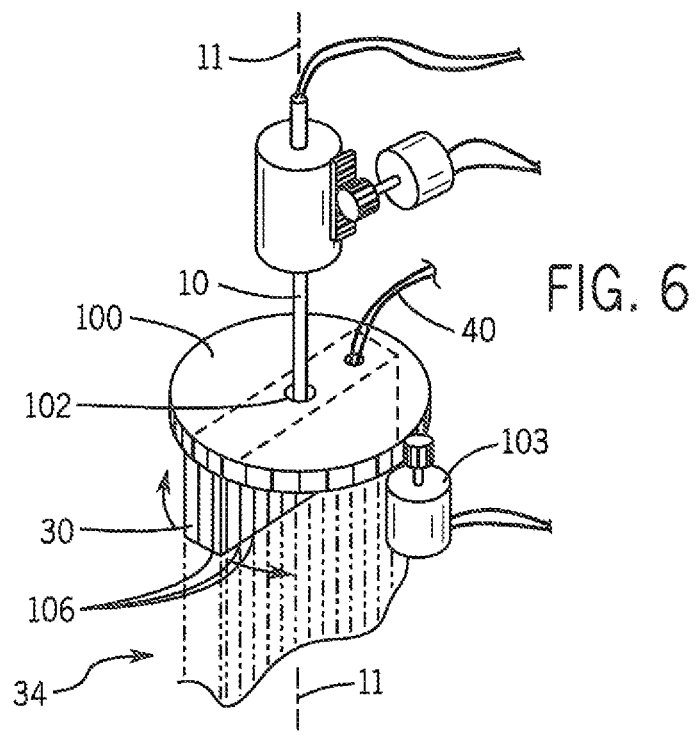
FIG. 6 is a simplified representation of an ultrasonic transducer for automatically acquiring data in the geometry shown in FIG. 2 by rotation of a 2-D ultrasound probe.

Referring now to FIG. 6, in one embodiment, movement of the ultrasonic transducer 30 may be automated by mounting a one-dimensional or 1.5 D ultrasonic transducer 30 on an axially reciprocating carriage 100, for example, driven by electric actuator 103 under the control of controller 46 (shown in FIG. 1). The transducer 30 may provide, for example, one (for a one-D probe) or a small number, such as three, rows of ultrasonic elements 106 (for a 1.5-D probe) each of which may be separately actuated for phased array or other imaging modes to transmit portions of the ultrasound beam 36 and to be independently readable to receive echo signals in return. The multiple rows of ultrasonic elements help provide for focusing of the ultrasound into a substantially planar ultrasound beam 36. The reciprocating carriage 100 may rotate the ultrasonic transducer 30 about axis 11 substantially mimicking the motion described above with respect to FIG. 1 while providing improved orientation of the resulting ultrasound beam 36 along the axis 11. The reciprocating action, for example, may move the ultrasonic transducer 30 by 180 degrees in one direction and then backward to its initial starting position to obtain the sheaf of data planes 34 described with respect to FIG. 2. A center of the ultrasonic transducer 30 may provide for an opening 102 through which the probe 10 may pass to permit for this improved orientation of the ultrasound beams 36 with the axis 11 while sacrificing only one center ultrasonic element 106 of the ultrasonic transducer 30 in an area which is generally oversampled. A simplified motorized carriage 52 is shown providing for vertical reciprocation along axis 11 of the probe 10 also under control of controller 46.

Figure 7:
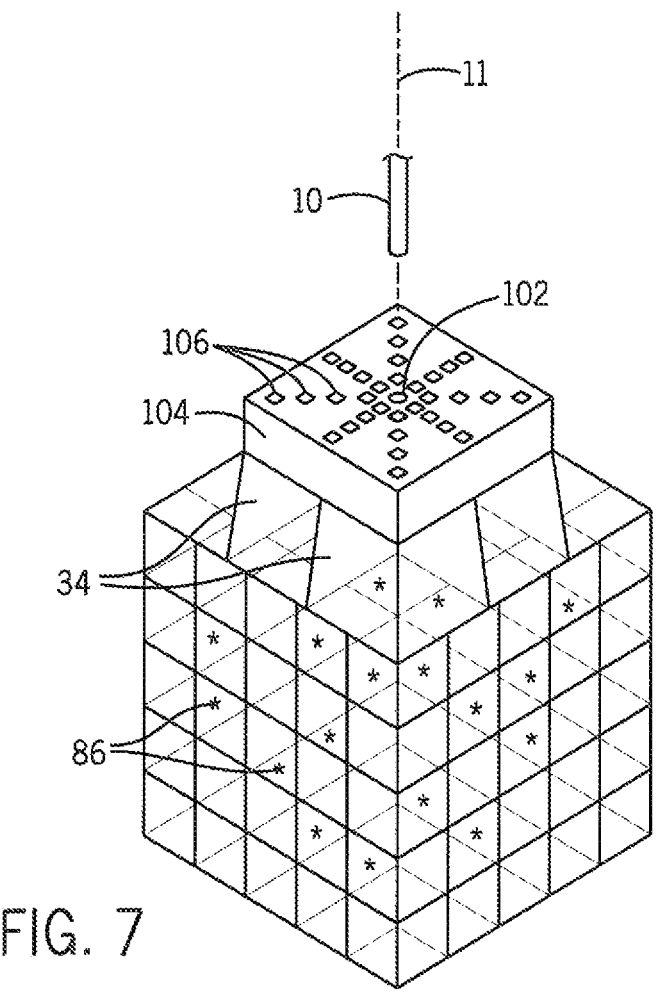
FIG. 7 is a figure similar to that of FIG. 6 showing a nonuniform 3-D ultrasonic probe for obtaining scattered data in the geometry of FIG. 2 such as is well accommodated by the present invention.

Referring now to FIG. 7, in an alternative embodiment, a modified two-dimensional array 104 may be created having scattered ultrasonic elements 106 positioned as needed for the acquisition of the multiple planes 34 without movement of the two-dimensional array 104. For example, the ultrasonic elements 106 may be placed along diagonal lines arrayed radially from axis 11 with a 45-degree spacing. This sparse ultrasound array reduces the number of channels necessary for data acquisition while still providing the rapid 3-D reconstruction of the present invention.

It will be appreciated that the spacing of the ultrasonic elements 106 along the lines perpendicular to the axis 11 of the ultrasonic elements 106 may be varied, for example, to reduce the element density toward the center of the array in favor of those ultrasonic elements 106 further outward for improved imaging resolution away from the center. The array 104 may be combined with the reciprocating carriage 100 to create a hybrid system.

It will be appreciated that the present invention may be combined with techniques to measure temperature of an ablated region, for example, as described in U.S. Pat. No. 7,166,075 hereby incorporated by reference. In this regard, the spatial data 86 may be generally scattered as in a cloud without regard to regular grid locations used for image display. The present invention is particularly suited for scattered and/or sparse data of this type allowing the location of the spatial data 86 to be freely acquired or readily tailored to regions of interest.

It will be appreciated that the present invention may be used advantageously with parametric imaging techniques on radiofrequency, or B-mode data, for 3-D quantitative ultrasound imaging. In addition, the invention can be used with color/power Doppler systems, for example, to produce a three-dimensional representation of blood flow. The invention is not limited to the probes described above and can be used, for example, with a planar, two-dimensional ultrasound array.

It will be further appreciated that the present invention may be used advantageously with standard imaging techniques such as B-mode, color and power Doppler imaging and the like for ablation techniques in which the simplification of the imaging acquisition provides for good reconstruction of ablation masses and for other high-speed 3-D visualization such as blood flow for 3-D vascular imaging. It will be appreciated that the invention is not limited to linear interpolation but also higher order (e.g. tricubic) interpolations may be used. Similarly the smoothness requirements can be enforced using the first derivative (first order finite differences) or higher order central differences.

It is specifically intended that the present invention not be limited to the embodiments and illustrations contained herein, but include modified forms of those embodiments including portions of the embodiments and combinations of elements of different embodiments as come within the scope of the following claims.

We claim:

1. A system for acquiring three-dimensional ultrasound data comprising:
an ultrasonic probe assembly including:
an ultrasonic probe providing an array of independently actuatable ultrasound elements having a predetermined spatial arrangement;
processing circuitry in communication with the ultrasonic probe to digitize echo signals received from the ultrasound elements, the ultrasonic probe and processing circuitry operating together to direct an ultrasound beam into a patient's tissue and receive ultrasonic echoes with respect to predetermined ultrasound elements and measure the same to provide ultrasound data at a plurality of first discrete locations related to the predetermined spatial arrangement of the predetermined ultrasound elements; and
an electronic computer receiving the ultrasound data and executing a stored program held in a non-transitive medium to:
(a) process the ultrasound data to obtain spatial data characterizing the tissue at the plurality of first discrete locations over three dimensions of a volume of interest within the tissue; and
(b) determine data of voxels in a plurality of second discrete locations in a three-dimensional image grid within the tissue by simultaneously minimizing a combination of:
an error between data of voxels and interpolated values of the spatial data in a region proximate to the data of voxels; and
a gradient of the data of the voxels at a location of each voxel,
wherein the region proximate to the spatial data extends in three dimensions about the spatial data by less than the volume of interest; and
(c) display an image comprising the spatial data and the data of voxels,
whereby a balance between interpolation fidelity and smoothness for human tissue is obtained in ultrasound measurements of the tissue.

2. The system of claim 1, wherein the error in interpolation is a function of a magnitude of a difference between a value of a given element of spatial data and an interpolated value of surrounding voxels to the plurality of first discrete locations of the spatial data in three dimensions.

3. The system of claim 1, wherein the gradient is a function of differences among data of voxels adjacent to a given voxel.

4. The system of claim 1, wherein the determination is performed by selecting a value of given voxel data to minimize:

$$\|Ac-b\|^2$$

subject to $$\|Bc\|^2 \le M$$

where: c is a vector of the data of the voxels to be determined;
b is a vector of the spatial data;
A is an interpolant matrix performing a linear interpolation of values c to locations of data points in b;
B is a finite differencing gradient matrix providing the gradient in data of the voxels; and
M is a constant selected to describe a desired image smoothness.

5. The system of claim 4, wherein A is a sparse matrix.

6. The system of claim 1, wherein the determination solves a closed form expression:

$$c=(A^TA+\lambda B^TB)^{-1}A^Tb$$

where:
c is the voxel data to be determined;
b is the spatial data surrounding the voxels;
A is an interpolant matrix performing a linear interpolation of values c to locations of data points in b;
B is a finite differencing gradient matrix providing the gradient in data of the voxels; and
$\lambda$ is a predetermined value controlling the amount of smoothing of the voxel data.

7. The system of claim 1, wherein a number of points of spatial data within the volume of interest is less than a number of voxels within the volume of interest.

8. The system of claim 1, wherein the region proximate to the spatial data extends to no more than closest eight voxels.

9. The system of claim 1, wherein the voxels are located at regular intervals along three Cartesian dimensions and the region proximate to the spatial data is a smallest polyhedron that surrounds the spatial data with voxels at vertex points and wherein the error is calculated only from interpolation from these vertex spatial data points.

10. The system of claim 9, wherein the interpolated values are trilinear interpolation in three dimensions.

11. The system of claim 1, wherein the volume of interest is subdivided into sub-blocks and step (b) is repeated for multiple sub-blocks and those multiple sub-blocks combined by weighting data at a periphery of adjacent sub-blocks.

12. The system of claim 1, wherein the spatial data characterizing the tissue is a speed of a shear wave through the tissue at points of spatial data.

13. The system of claim 12, further comprising a reciprocating carriage configured to move the ultrasonic probe assembly to generate the shear wave.

14. The system of claim 1, wherein the spatial data characterizing the tissue is a function of displacement of the tissue in response to a quasi-static periodic compression of the tissue.

15. The system of claim 1, further comprising an RF ablation probe configured to ablate the tissue.

16. A method of acquiring three-dimensional ultrasound data using an ultrasonic probe assembly including an ultrasonic probe providing an array of independently actuatable ultrasound elements having a predetermined spatial arrangement, and processing circuitry in communication with the ultrasonic probe to digitize echo signals received from the ultrasound elements, the ultrasonic probe and processing circuitry operating together to direct an ultrasound beam into a patient's tissue and receive ultrasonic echoes with respect to predetermined ultrasound elements and measure the same to provide ultrasound data at a plurality of first discrete locations related to the predetermined spatial arrangement of the predetermined ultrasound elements, comprising the following steps executed on an electronic computer receiving the ultrasound data and executing a stored program held in a non-transitive medium to:
(a) process the ultrasound data to obtain spatial data characterizing the tissue at the plurality of first discrete locations over three dimensions of a volume of interest within the tissue; and (b) determine data of voxels in a plurality of second discrete locations in a three-dimensional image grid within the tissue by simultaneously minimizing a combination of:

an error between data of voxels and interpolated values of the spatial data in a region proximate to the spatial data; and a gradient of the data of the voxels at a location of the given voxel;

wherein the region proximate to the spatial data extends in three dimensions about the spatial data by less than the volume of interest; and (c) display an image comprising the spatial data and the data of voxels, whereby a balance between interpolation fidelity and smoothness for human tissue is obtained in ultrasonic measurements of the tissue.

17. The method of claim 16, wherein the determination is performed by selecting a value of data of a given voxel to minimize:

$$\|Ac-b\|^2$$

subject to $$\|Bc\|^2 \leq M$$

where:
c is the voxel data to be determined;
b is the spatial data proximate to the voxels;
A is an interpolant matrix performing a linear interpolation of values c to locations of data points in b; and
B is a finite differencing gradient matrix providing the gradient in data of the voxels; and
M is a constant selected to describe a desired image smoothness.

18. The method of claim 17, wherein A and B are both sparse matrices.

19. The method of claim 17, wherein the determination solves the closed form expression:

$$c=(A^T A+\lambda B^T B)^{-1} A^T b$$

where:
c is the voxel data to be determined;
b is the spatial data proximate to the voxels;
A is an interpolant matrix performing a linear interpolation of values b to a location of c;
B is a finite differencing gradient matrix providing the gradient in data of the voxels; and
$\lambda$ is a predetermined value controlling the amount of smoothing of the voxel data.

20. The method of claim 16, wherein a number of points of spatial data within the volume of interest is less than a number of voxels within the volume of interest.

21. The method of claim 16, wherein the region proximate to the spatial data extends only to closest eight voxels.

* * * * *